Figure 1:
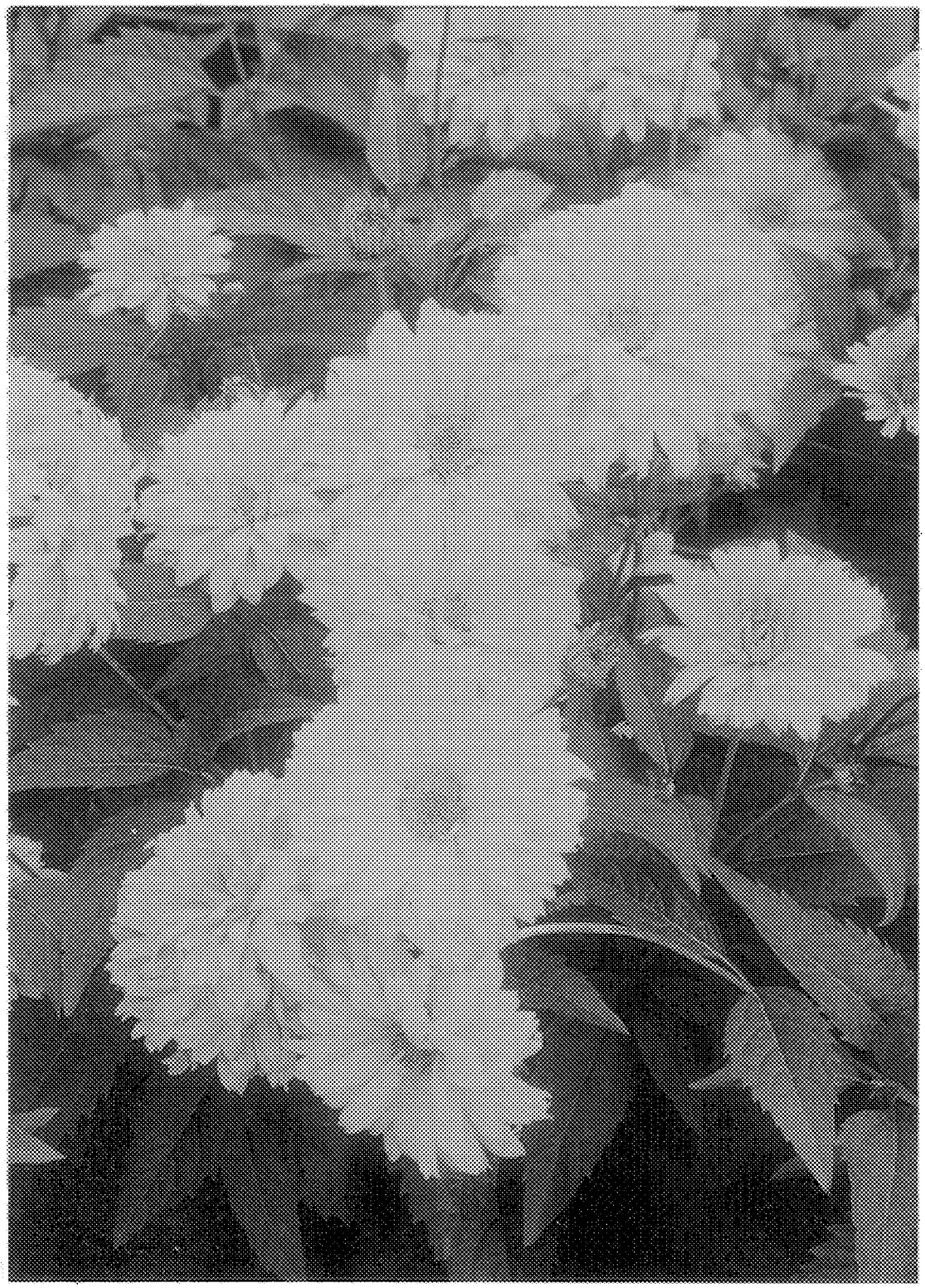

US00PP11270P

United States Patent [19]

Bloom

[11] Patent Number: Plant 11,270

[45] Date of Patent: Mar. 7, 2000

[54] HELIOPSIS PLANT NAMED 'BRESSINGHAM DOUBLOON'

[75] Inventor: Alan Bloom, Norfolk, United Kingdom

[73] Assignee: Blooms of Bressingham Ltd., Norfolk, United Kingdom

[21] Appl. No.: 08/907,934

[22] Filed: Aug. 11, 1997

[51] Int. Cl.[7] ..... A01H 5/00

[52] U.S. Cl. ..... Plt./263

[58] Field of Search ..... Plt./54.1, 68.1, Plt./263

[56] References Cited

U.S. PATENT DOCUMENTS

P.P. 10,690 11/1998 Hanson ..... Plt./263

*Primary Examiner*—Howard J. Locker
*Assistant Examiner*—Kent L. Bell
*Attorney, Agent, or Firm*—Foley & Lardner

[57] ABSTRACT

A new and distinct cultivar of Heliopsis plant named 'Bressingham Doubloon' characterized by its semi-double golden yellow flowers which commence in late July and continue to early September, and its vigorous growth habit, with erect branched stems carrying large lanceolate leaves.

2 Drawing Sheets

The present invention relates to a new and distinct cultivar of hardy perennial herbaceous plant of the genus Heliopsis, known by the cultivar name 'Bressingham Doubloon'. The genus is a member of the Compositae family.

The new cultivar originated as a seedling discovered by the inventor Alan Bloom in Bressingham, Diss, Norfolk, England. The seedling resulted from a cross made by the inventor between a cultivar of Heliopsis *helianthoides scabra* named 'Desert King' (unpatented) as the seed parent, and an unknown pollen parent.

The first act of asexual reproduction of 'Bressingham Doubloon' was accomplished when cuttings were taken by the inventor in Bressingham, Diss, Norfolk, England in 1988. This and subsequent asexual reproduction have shown that the unique combination of characteristics as herein disclosed for 'Bressingham Doubloon' are fixed and retained through successive generations of asexual reproduction.

'Bressingham Doubloon' has not been observed under all possible environmental conditions. The phenotype may vary with variations in environment such as temperature and light intensity without, however, any variance in the genotype.

The following observations and measurements describe plants grown in Bressingham, Diss, Norfolk, England under normal commercial practice. All color values are based on The Royal Horticulture Society (R.H.S.) colour charts.

The following traits have been repeatedly observed and are determined to be basic characteristics of the new cultivar, which in combination distinguish the new cultivar from others:

1. It is a quality flowering perennial with excellent golden yellow flower color combined with colored stems, good foliage, and a vigorous and healthy, bushy growth habit.
2. The large and full semi-double flowers are carried by erect leafy stems and are arranged in cymes.
3. The branched stems carry large lanceolate leaves which offer a pleasing backdrop to the many large golden yellow flowers.
4. The plant thrives best in full sun and well drained soil, and seldom requires staking.
5. Flowering commences in late July and continues to early September. This, combined with its robust growth habit, makes the cultivar ideal for use in borders.

Figure 2:
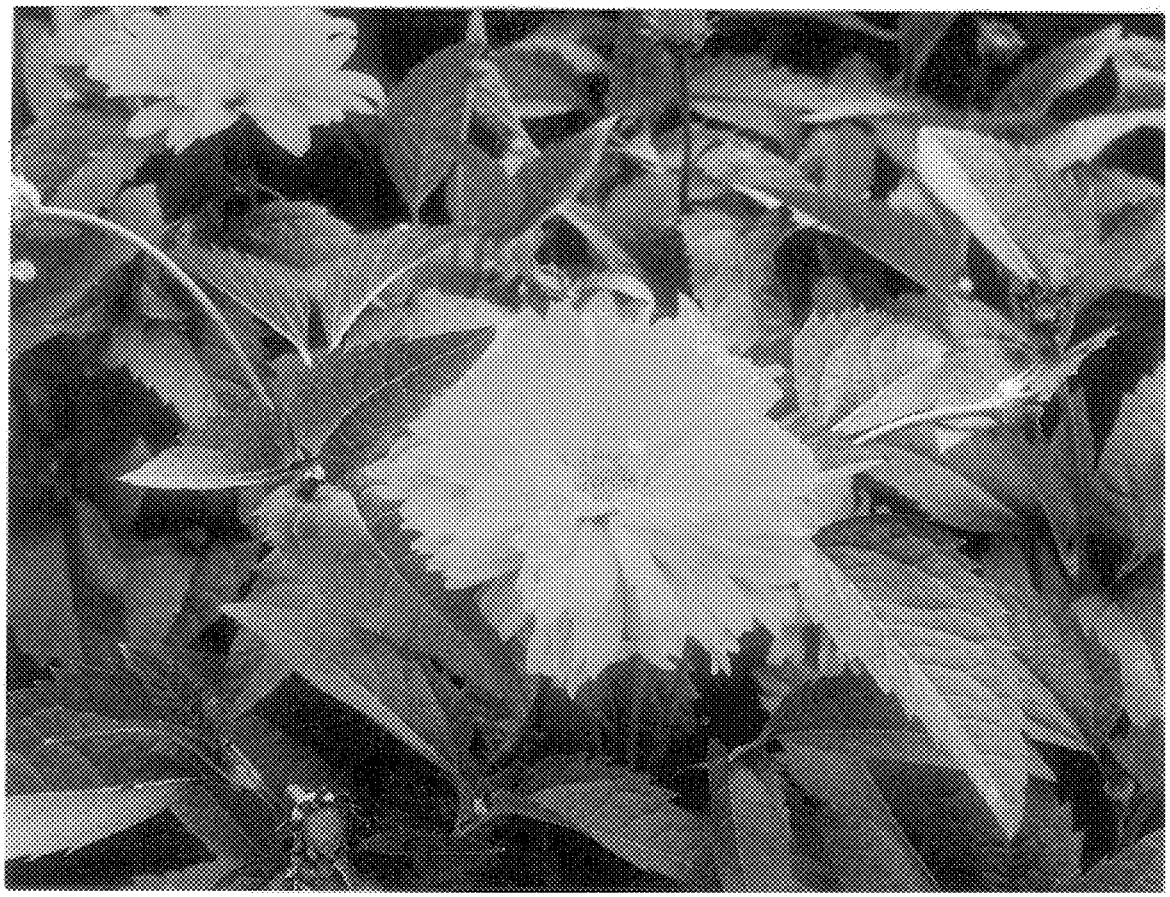

In the photographic drawings, FIG. 1 comprises a closeup view of a typical plant of 'Bressingham Doubloon', showing in detail the foliage and the large and full semi-double golden yellow flowers. The photograph comprising FIG. 2 emphasizes the branched leafy stems and the vigorous bushy habit of the new cultivar.

DETAILED PLANT DESCRIPTION

Parentage: A cross between a cultivar of *Helianthoides scabra* named 'Desert King' (seed parent) and an unknown pollen parent.

Habit: Branching, erect leafy stems create a dense bushy habit.

Size: Mature plants are 100 cm to 150 cm in height with a spread of 45 cm.

Root system: Fibrous.

Plant vigor: A perennial that shows vigorous and healthy growth through Great Britain.

Blooming habit: The flowers are borne on erect leafy flower stems that arise from the base of the plant; approximately 40 blooms per plant.

Blooming period: Approximately 8 weeks, from late July continuing into early September.

*Lasting quality of bloom.*—The cultivar will display blooms for all of the blooming period, approximately 8 weeks. As cut flowers, they have not been trialled.

Hardiness: Winter hardy throughout the British Isles. The plant has not been fully tested for maximum summer tolerance above 32 C. (90 F.).

Foliage:

*Shape.*—Lanceolate, serrated.
*Texture.*—Upper surface scabrous.
*Length.*—10 cm to 15 cm.
*Width.*—5 cm to 8 cm.
*Petiole length.*—0.5 cm.
*Margins.*—Serrate.
*Apex.*—Apiculate.
*Base.*—Cordate.
*Color.*—Mature leaves, upper surface 137A, under surface 137B.

Inflorescence:

*Borne.*—Cymes, simple.
*Capitulum.*—Height is up to a maximum of 1 cm and the diameter is 8 to 10 cm. The diameter of the disc is 2 cm.
*Ray florets.*—Approximately 40 per inflorescence, of similar size; shape is oblong and the ends are slightly ruffled; 4 to 5 cm in length; color of upper surface is yellow-orange, R.H.S. 21 A; color of under surface is yellow-orange, R.H.S. 21 C.
*Disc florets.*—Densely clustered; numerous in quantity; no seed has been collected; color of upper surface is yellow-orange, R.H.S. 21 C; color of under surface is yellow-orange, R.H.S. 21 C.

*Peduncle.*—Up to 20 cm in length, stiff, green, R.H.S. 137 C.

*Sepals.*—Lanceolate in shape and arranged as an outer whorl around the flower head, are most evident before the ray florets have fully developed or elongated.

*Bud.*—Before they begin to open, bud is green in color, R.H.S. 138 C; as the bud begins to open, the ray florets can be seen forming; the color at this time is yellow-green, R.H.S. 154 C.

*Carpels.*—1 celled.

*Stamens.*—Epipetalous.

*Fragrance.*—None.

I claim:

1. A new and distinct cultivar of Heliopsis plant named 'Bressingham Doubloon', substantially as shown and described.

* * * * *